April 6, 1976 E. D. WILLIAMS Plant Pat. 3,860
ROSE PLANT
Filed April 22, 1975
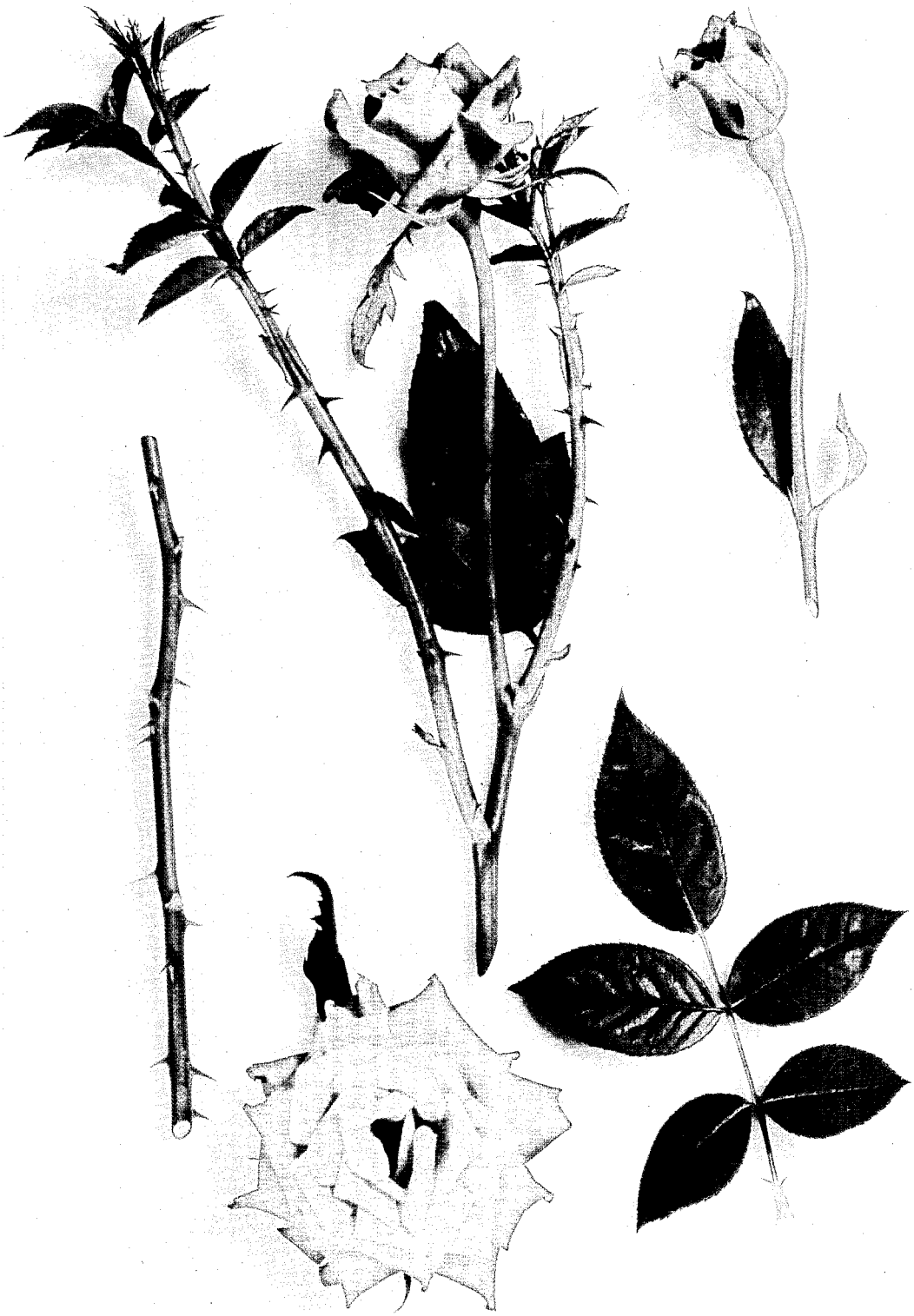

United States Patent

Plant Pat. 3,860

Patented Apr. 6, 1976

3,860

ROSE PLANT

Ernest D. Williams, 1510 Lebanon Ave., Dallas, Tex. 75208

Filed Apr. 22, 1975, Ser. No. 570,513

Int. Cl. A01h *5/00*

U.S. Cl. Plt.—7 1 Claim

The present invention relates to a new and distinct variety of hardy, dwarf, bush type rose plant of the miniature class; the variety being primarily characterized, as to novelty, by well shaped pink buds which in general color effect are deep pink on upper surface with a lighter pink on outer surface, the bud and flower being similar in form to Windy City (miniature—plant patent pending).

The variety is further characterized by:

An abundance of flowers which are borne singly or several to the stem in loose clusters.

Slight fragrance.

A plant which is vigorous, of upright, compact growth and with moderately small, glossy foliage with pointed leaflets. The plant which has a normal height of 12 to 14 inches may be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Dallas, Tex., under conditions of careful control and observation, as a cross between Little Darling (floribunda—Plant Pat. No. 1,581) as the seed parent and Over the Rainbow (Plant Pat. No. 3,472—miniature) as the pollen parent.

Subsequent to origination of the variety I successfully asexually reproduced it, in my nursery located at Dallas, Tex., by cuttings, the reproductions having run true in all respects.

The color photo illustrates the variety, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bush; seedling; greenhouse; outdoors; cut flowers; garden decoration.

Class: Miniature.

Flowers: Continuity profuse—with repeat bloom all season. Fragrance; soft, sweet.

Flowers borne: Singly and several together on strong, medium length stems.

Quantity of bloom: Abundant.

Bud: Peduncle; long; slender but sturdy; erect; medium green, sometimes tinted bronze; hairs, few, very short. Before calyx breaks; size—small. Form medium long, pointed; few foliaceous appendages and few or no hairs on surface of bud; with foliaceous parts extending beyond the tip of the bud equal one half or less of its length. Color; medium green, sometimes tinted with bronze. As calyx breaks: color—pink to red. As first petal opens: light pink underlaid with white—inside surface deep pink.

Bloom: Size when fully open—small, averaging about 1½ inches. Petalage: double—25 to 30 petals, arranged regularly. Form: high centered; petals roll out and downward at maturity. Edges of petals tend to fold back.

Petals: Fairly thick; satiny both inside and outside. Shape: Outside petals — broad lanceolate (nearly round) with acute tip. Intermediate: broad lanceolate with acute tip. Inside: lanceolate to broad lanceolate with acute tip.

Color: Newly opened flower from a plant grown in plastic greenhouse, April 1975.

*Outside petal.*—Outside surface.—Neyron Rose 623/2 to Neyron Rose 623/3 shading lighter on lower one half of petal and blending into soft yellow at base. Inside surface: White overlaid with deep Tyrian Rose, near 24/2 but modified with magenta to give appearance of deep pink, then shading into a white zone thence into yellow at base of petal.

*Intermediate petal.*—Outside surface—Tyrian Rose 24/3 on upper ¼ to ⅓ of petal then shading into yellow becoming deeper yellow at base. Inside surface: white or yellowish overlaid with Tyrian Rose 24 to 24/1 on upper ½ or more of petal then shading into yellow at base.

*Inner petal.*—Outside surface—soft yellow on lower one half then blending into white overlaid with Tyrian Rose 24/3 near tip. Inside surface—similar to intermediate petal. General color effect newly opened flowers: pink with a soft blending of white and yellow. Three days open: similar color but pink may be deeper and the yellow has lightened or become white. Behavior: as flowers age petals may become darker shade before dropping off. Flower longevity: April 1975; plant in pot—5 to 7 days. Cut blooms at living room temperature, 4 to 5 days or longer.

Reproductive organs:

*Stamens.*—Average, arranged regularly about pistil.

*Filaments.*—Short, yellow.

*Pollen.*—Fair amount.

*Pistils.*—Average number.

*Styles.*—Uneven, short, bunched, color—red.

*Stigma.*—Near white to yellowish.

*Ovaries.*—All enclosed in calyx.

*Hips.*—None.

*Sepals.*—Permanent, spear shaped, fold downward and outward.

*Seeds.*—None.

Foliage:

*Leaves.* — Compound of five leaflets, sometimes three; average abundance, moderately small; leathery; glossy.

Leaflets:

*Shape.*—Lanceolate to broad lanceolate, apex acute, base rounded, margin serrate.

*Color.*—Normal green; new growth often tinted bronze or reddish.

*Rachis.*—Medium strength; upper side grooved; few tiny hairs; underside sparsely thorny with few tiny prickles.

*Stipules.*—fairly long, medium width; medium length narrow points which turn out at about 45 degree angle.

Growth:

*Habit.*—Dwarf, bushy, upright.

*Growth.*—Free, vigorous.

*Canes.*—Medium; slender.

*Main stems.*—Color—medium green, sometimes reddish. Thorns, few; color, brown. Prickles few or none. Hairs, none.

*Branches.*—Color—medium green. Thorns, few or none. Prickles, none. Hairs, none.

*New shoots.* — Color — medium green, sometimes tinted reddish or bronze. Thorns, few or none. Prickles, none. Hairs, none.

The miniature rose plant and its flowers as herein described may vary in slight detail due to climatic, soil and cultural conditions under which the variety may be grown; the present description being of the variety as grown at Visalia, Calif., and which is substantially the same as grown outdoors at Dallas, Tex.

The following is claimed:

1. A new and distinct variety of miniature rose plant of hardy, dwarf, much branched, bush type, as illustrated and described, characterized by buds and flowers resembling the Windy City miniature rose (plant patent pending) in general form of bud but less double flower, the color being a lighter shade of pink with yellow at base of both inside and outside petal surfaces, the general color effect being pink with the reverse (outer) side of petals being a lighter pink blended with yellow; and further characterized by a plant which is of vigorous and compact habit but more restrained in growth than Windy City, easy to propagate from cuttings; with small glossy foliage, often tinted reddish or bronze on new growth; with flowers borne singly or several to stem in loose clusters.

No references cited.

ROBERT E. BAGWILL, Primary Examiner

UNITED STATES PATENT OFFICE

CERTIFICATE OF CORRECTION

Patent No. PP 3,860 Dated April 6, 1976

Inventor(s) Ernest D. Williams

It is certified that error appears in the above-identified patent and that said Letters Patent are hereby corrected as shown below:

The present drawing should be canceled and the attached drawing substituted therefor as part of the Letters Patent.

Signed and Sealed this

Twenty-third Day of November 1976

[SEAL]

*Attest:*

RUTH C. MASON
*Attesting Officer*

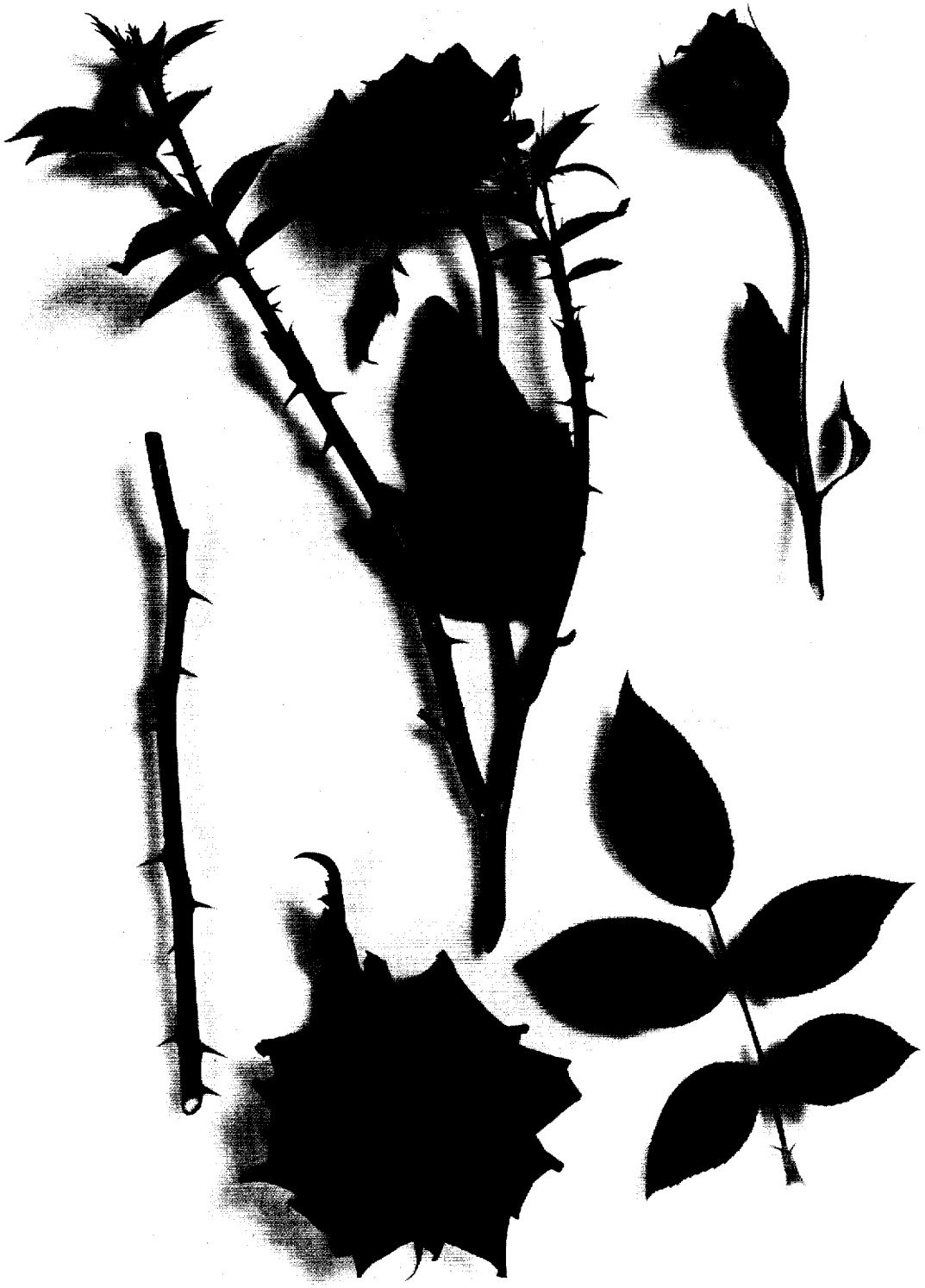

C. MARSHALL DANN
*Commissioner of Patents and Trademarks*